United States Patent [19]
Lee et al.

[11] Patent Number: 6,004,578
[45] Date of Patent: Dec. 21, 1999

[54] PERMEATION ENHANCES FOR TRANSDERMAL DRUG DELIVERY COMPOSITIONS, DEVICES AND METHODS

[75] Inventors: Eun Soo Lee, Redwood City; Su Il Yum, Los Altos, both of Calif.

[73] Assignee: ALZA Corporation, Palo Alto, Calif.

[21] Appl. No.: 08/956,379

[22] Filed: Oct. 23, 1997

Related U.S. Application Data

[60] Provisional application No. 60/030,424, Oct. 24, 1996.

[51] Int. Cl.$^6$ .................................................. A61F 13/02
[52] U.S. Cl. ......................... 424/448; 424/443; 424/444; 424/447; 424/449; 514/946; 514/947
[58] Field of Search .................. 514/946, 947; 424/443, 444, 447, 448, 449

[56] References Cited

U.S. PATENT DOCUMENTS

| | | | |
|---|---|---|---|
| 3,472,931 | 10/1969 | Stoughton | 424/180 |
| 3,527,864 | 9/1970 | Kilmer et al. | 424/177 |
| 3,598,123 | 8/1971 | Zaffaroni | 128/268 |
| 3,731,663 | 5/1973 | Zaffaroni | 128/268 |
| 3,797,494 | 3/1974 | Zaffaroni | 128/268 |
| 3,896,238 | 7/1975 | Smith | 424/358 |
| 3,903,256 | 9/1975 | MacMillan et al. | 424/59 |
| 3,952,099 | 4/1976 | Smith | 424/227 |
| 4,046,886 | 9/1977 | Smith | 424/227 |
| 4,130,643 | 12/1978 | Smith | 424/238 |
| 4,130,667 | 12/1978 | Smith | 424/361 |
| 4,144,317 | 3/1979 | Higuchi et al. | 424/21 |
| 4,286,592 | 9/1981 | Chandrasekaran | 128/260 |
| 4,299,826 | 11/1981 | Luedders | 424/181 |
| 4,314,557 | 2/1982 | Chandrasekaran | 128/260 |
| 4,335,115 | 6/1982 | Thompson et al. | 424/181 |
| 4,343,798 | 8/1982 | Fawzi | 424/240 |
| 4,379,454 | 4/1983 | Campbell et al. | 604/897 |
| 4,405,615 | 9/1983 | Rajadhyaksha | 424/244 |
| 4,435,180 | 3/1984 | Leeper | 604/896 |
| 4,559,222 | 12/1985 | Enscore et al. | 424/28 |
| 4,568,343 | 2/1986 | Leeper et al. | 604/896 |
| 4,573,999 | 3/1986 | Netto | 623/7 |
| 4,645,502 | 2/1987 | Gale et al. | 604/896 |
| 4,704,282 | 11/1987 | Campbell et al. | 424/449 |

(List continued on next page.)

FOREIGN PATENT DOCUMENTS

| | | |
|---|---|---|
| 1011949 | 12/1965 | United Kingdom . |
| WO92/20378 | 11/1992 | WIPO . |
| WO 95/09006 | 4/1995 | WIPO . |
| WO96/19976 | 7/1996 | WIPO . |
| WO96/40139 | 12/1996 | WIPO . |

OTHER PUBLICATIONS

Williams, A.C., et al., Critical Reviews in Therapeutic Drug Carrier Systems, 9 (3,4), pp. 305–353 (1992), "Skin Absorption Enhancers".

Santus, G.C., et al., Journal of controlled Release, 25 (1993) pp. 1–20, "Transdermal Enhancer Patent Literature".

Kadir et al., J. Pharma. Sci. 1989, 78 (2): 149–153 Generation of Theophylline and Adenosine into Excised Human Skin from Binary and Ternary Vehicles: Effect of a Nonionic Surfactant.

*Primary Examiner*—S. Mark Clardy
*Assistant Examiner*—Michael A. Williamson
*Attorney, Agent, or Firm*—Michael J. Rafa; Steven F. Stone

[57] ABSTRACT

The present invention is directed to the transdermal administration of at least one drug together with a suitable amount of a permeation enhancer comprising monoalkyl ethers of polyethyleneglycol and their alkyl or aryl carboxylic acid esters and carboxymethyl ethers. The invention includes a transdermal drug delivery device comprising a matrix adapted to be placed in drug- and- permeation enhancer-transmitting relation with a skin site. The matrix contains sufficient amounts of the permeation enhancer and drug, in combination, to continuously administer drug to the systemic circulation of a patient at a therapeutically effective rate. The invention is also directed to compositions and methods for transdermal administration of at least one drug together with a permeation enhancer of this invention, alone or in combination with other enhancers.

34 Claims, 15 Drawing Sheets

U.S. PATENT DOCUMENTS

| | | | |
|---|---|---|---|
| 4,746,515 | 5/1988 | Cheng et al. | 424/449 |
| 4,764,379 | 8/1988 | Sanders et al. | 424/449 |
| 4,788,062 | 11/1988 | Gale et al. | 424/449 |
| 4,816,258 | 3/1989 | Nedberge et al. | 424/448 |
| 4,820,720 | 4/1989 | Sanders et al. | 514/356 |
| 4,849,226 | 7/1989 | Gale | 424/448 |
| 4,863,738 | 9/1989 | Taskovich | 424/449 |
| 4,863,970 | 9/1989 | Petal et al. | 514/784 |
| 4,865,848 | 9/1989 | Cheng et al. | 424/449 |
| 4,900,555 | 2/1990 | Cheng et al. | 424/449 |
| 4,908,027 | 3/1990 | Enscore et al. | 604/890 |
| 4,940,586 | 7/1990 | Cheng et al. | 424/464 |
| 4,943,435 | 7/1990 | Baker et al. | 424/448 |
| 4,973,468 | 11/1990 | Chiang et al. | 424/424 |
| 5,004,610 | 4/1991 | Oisborne et al. | 424/448 |
| 5,053,327 | 10/1991 | Chiang et al. | 424/448 |
| 5,059,426 | 10/1991 | Chiang et al. | 424/449 |
| 5,314,694 | 5/1994 | Gale et al. | 424/448 |
| 5,378,730 | 1/1995 | Lee et al. | 514/535 |
| 5,411,740 | 5/1995 | Lee et al. | 424/448 |
| 5,413,776 | 5/1995 | Suzuki et al. | 424/448 |
| B1 3,598,122 | 11/1982 | Zaffaroni | 128/268 |
| B1 4,588,580 | 1/1989 | Gale et al. | 424/21 |

PERMEATION ENHANCES FOR TRANSDERMAL DRUG DELIVERY COMPOSITIONS, DEVICES AND METHODS

This Application claims benefit of Provisional Application No. 60/030,424 Oct. 24, 1996.

FIELD OF THE INVENTION

This invention relates to the transdermal delivery of drugs and more particularly to permeation enhancers for compositions, devices, and methods for enhancing the percutaneous absorption of drugs when administered to a body surface or membrane. The permeation enhancers of this invention comprise monoalkyl ethers of polyethyleneglycol and their alkyl or aryl carboxylic acid esters and carboxymethyl ethers. The permeation enhancers of this invention are used either alone or in combination with other permeation enhancers.

DESCRIPTION OF TERMS

As used herein, the term "drug" is to be construed in its broadest sense to mean any material which is intended to produce some biological, beneficial, therapeutic, or other intended effect, such as permeation enhancement, for example, on the organism to which it is applied.

As used herein, the term "transdermal" refers to the use of skin, mucosa, and/or other body surfaces as a portal for the administration of drugs by topical application of the drug thereto.

As used herein, the term "therapeutically effective" amount or rate refers to the amount or rate of drug needed to effect the desired therapeutic result.

As used herein, the phrase "sustained time period" intends at least about 12 hours and will typically intend a period in the range of about one to about seven days.

As used herein, the term "individual" intends a living mammal and includes, without limitation, humans and other primates, livestock and sports animals such as cattle, pigs and horses, and pets such as cats and dogs.

As used herein, the phrase "predetermined area of skin" intends a defined area of intact unbroken skin or mucosal tissue. That area will usually be in the range of about 5 $cm^2$ to about 100 $cm^2$.

As used herein, the term "permeation enhancer" intends an agent or a mixture of agents which, alone or in combination, acts to increase the permeability of the skin to a drug.

As used herein, the term "permeation enhancement" intends an increase in the permeability of skin to a drug in the presence of a permeation enhancer as compared to permeability of skin to the drug in the absence of a permeation enhancer.

As used herein, the term "permeation-enhancing" intends an amount or rate of a permeation enhancer which provides permeation enhancement throughout a substantial portion of the administration period.

BACKGROUND OF THE INVENTION

The transdermal route of parenteral delivery of drugs provides many advantages, and transdermal systems for delivering a wide variety of drugs are described in U.S. Pat. Nos. 3,598,122; 3,598,123; 3,731,683; 3,797,494; 4,286, 592; 4,314,557; 4,379,454; 4,435,180; 4,559,222; 4,568, 343; method U.S. Pat. Nos. 4,573,999; 4,588,580; 4,645, 502; 4,704,282; 4,816,258; 4,849,226; 4,908,027; 4,943, 435; 5,004,610; 5,314,694; and U.S. Pat. No. 5,411,740, for example, all of which are incorporated herein by reference. In many cases, drugs which would appear to be ideal candidates for transdermal delivery are found to have such low permeability through intact skin that they cannot be delivered in therapeutically effective amounts from reasonably sized devices.

In an effort to increase skin permeability so that drugs can be delivered in therapeutically effective amounts, it has been proposed to pretreat the skin with various chemicals or to concurrently deliver the drug in the presence of a permeation enhancer. Various materials have been suggested for this, as described in U.S. Patent Nos. 3,472,931; 3,527,864; 3,896, 238; 3,903,256; 3,952,099; 4,046,886; 4,130,643; 4,130, 667; 4,299,826; 4,335,115; 4,343,798; 4,379,454; 4,405, 616; 4,568,343; 4,746,515; 4,764,379; 4,788,062; 4,820, 720; 4,863,738; 4,863,970; 4,865,848; 4,900,555; 4,940, 586; 4,973,468; 5,053,227; 5,059,426; 5,378,730; WO 95/09006; and British Pat. No. 1,011,949, all of which are hereby incorporated in their entirety by reference. Williams et al. "Skin Absorption Enhancers" *Critical Review in Therapeutic Drug Carrier Systems*, pp. 305–353 (1992) and Santus et al. "Transdermal Enhancer Patent Literature", *Journal of Controlled Release*, pp. 1–20 (1993) also provide a recent review of transdermal permeation enhancers.

To be considered useful, a permeation enhancer should have the ability to enhance the permeability of the skin for at least one and preferably a significant number of drugs. More importantly, it should be able to enhance the skin permeability such that the drug delivery rate from a reasonably sized system (preferably 5–60 $cm^2$) is at therapeutically effective levels. Additionally, the enhancer when applied to the skin surface, should be non-toxic, non-irritating on prolonged exposure and under occlusion, and non-sensitizing on repeated exposure. Preferably, it should be odorless, physiologically inactive, and capable of delivering drugs without producing burning or tingling sensations.

In addition to these permeation enhancer-skin interaction considerations, a permeation enhancer must also be evaluated with respect to possible interactions within the transdermal system itself. For example, the permeation enhancer must be compatible with the drug to be delivered, the adhesive, and the polymer matrix in which the drug is dispersed. The permeation enhancer should also be selected so as to ensure a suitable balance among tack, adhesion, and cohesive strength of the adhesive.

SUMMARY OF THE INVENTION

According to the present invention, it has been discovered that monoalkyl ethers of polyethyleneglycol and their alkyl or aryl carboxylic acid esters and carboxymethyl ethers, either alone or in combination with other permeation enhancers, enhance the permeability of the skin to transport of drugs therethrough. In addition, the combined effect of a permeation enhancer according to this invention with other permeation enhancers known in the art such as monoglycerides of fatty acids and ethanol provides a surprising, i.e. more than additive, increase in the transdermal flux of drug. The invention provides novel compositions for use with transdermal drug delivery devices and methods for effectively administering drugs and greatly increasing the drug permeability through the skin while reducing the lag time between application of the drug to the skin and attainment of the desired therapeutic effect.

Therefore, it is an object of the present invention is to provide improved drug delivery by means of transdermal systems and compositions.

A further object is to increase the transport of drugs across the skin following application of a transdermal therapeutic system.

Another object is to eliminate the lag time between the application of a transdermal therapeutic system and attainment of the desired therapeutic flux level.

Accordingly, the present invention provides compositions and devices for transdermal administration of at least one drug to the systemic circulation of a patient, at a therapeutically effective rate, by permeation through a body surface or membrane, comprising at least one drug and a permeation-enhancing amount of a permeation enhancer selected from monoalkyl ethers of polyethyleneglycol and their alkyl or aryl carboxylic acid esters and carboxymethyl ethers, either alone or in combination with other permeation enhancers. The invention further provides a method for the transdermal coadministration of a drug at a therapeutically effective rate together with a skin permeation-enhancing amount of the permeation enhancer.

The system of the invention is preferably a transdermal drug delivery device comprising a matrix adapted to be placed in drug- and permeation enhancer-transmitting relation with a body surface or membrane such as the skin or mucosa. The system must be of a reasonable size useful for the application of the drug and the enhancer to a human body.

DETAILED DESCRIPTION OF THE INVENTION

Figure 1:
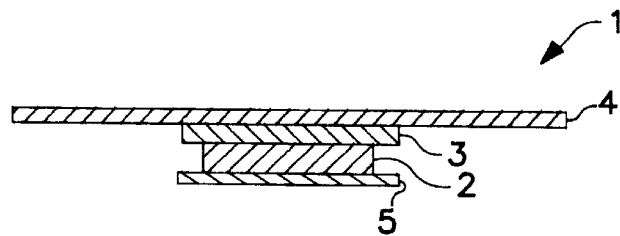
FIG. 1 is a cross-sectional view of one embodiment of a transdermal therapeutic drug delivery device which may be used in accordance with the present invention.

According to this invention, it has been discovered that monoalkyl ethers of polyethyleneglycol and their alkyl or aryl carboxylic acid esters and carboxymethyl ethers, either alone or in combination with other permeation enhancers, substantially increase the permeability of a body surface or membrane to transport of at least one drug therethrough. Additionally, the combination of the permeation enhancers according to this invention with other permeation enhancers known in the art, such as ethanol and monoglycerides, provides a synergistic effect on the transdermal flux of a drug. The permeation enhancers of this invention can be used to effectively enhance the permeability of drugs through body surfaces or membranes in general and particularly through the skin.

The monoalkyl ethers of polyethyleneglycol and their alkyl or aryl carboxylic acid esters and carboxymethyl ethers of this invention are represented by the following formula:

$$CH_3(CH_2)_n(OCH_2CH_2)_m—OR \qquad (I)$$

wherein n=3–19; m=1–20; and R=i) H; ii) $CH_2COOH$; or iii) OC—R' where R' is an alkyl or aryl group comprising 1–16 carbons. Preferably, the permeation enhancer is selected from polyethyleneglycol monolauryl ethers and their alkyl or aryl carboxylic acid esters and carboxymethyl ethers. Preferred enhancers according to this invention include diethylene glycol monododecyl ether, tetraethylene glycol monododecyl ether, diethylene glycol monododecyl ether acetate, diethylene glycol monododecyl ether benzoate, triethylene glycol monododecyl ether carboxylic acid, and polyethylene glycol monododecyl ether carboxylic acid.

The permeation enhancers according to this invention may be used alone or in combination with other permeation enhancers known in the art, including, but not limited to, monoglycerides or mixtures of monoglycerides of fatty acids such as glycerol monolaurate, glycerol monooleate, and glycerol monolinoleate, lauramide diethanolamine, lower $C_{1-4}$ alcohols, alkyl laurates such as methyl laurate, acyl lactylates, dodecyl acetate, and $C_{10}$–$C_{20}$ fatty acid esters including lactic acid esters such as lauryl lactate, myristyl lactate, and cetyl lactate. A preferred embodiment is directed to the use of a permeation enhancer according to Formula I in combination with ethanol or a monoglyceride of a fatty acid, such as glycerol monolaurate or glycerol monooleate.

The examples that follow demonstrate the utility of the permeation enhancers of this invention for several dissimilar drugs. It is believed that this invention has utility in connection with the delivery of drugs within the broad class normally delivered through body surfaces and membranes, including skin. In general, this includes therapeutic agents in all of the major areas, including, but not limited to, ACE inhibitors, adenohypophoseal hormones, adrenergic neuron blocking agents, adrenocortical steroids, inhibitors of the biosynthesis of adrenocortical steroids, alpha-adrenergic agonists, alpha-adrenergic antagonists, selective alpha-two-adrenergic agonists, analgesics, antipyretics and anti-inflammatory agents, androgens, local and general anesthetics, antiaddictive agents, antiandrogens, antiarrhythmic agents, antiasthmatic agents, anticholinergic agents, anticholinesterase agents, anticoagulants, antidiabetic agents, antidiarrheal agents, antidiuretic, antiemetic and prokinetic agents, antiepileptic agents, antiestrogens, antifungal agents, antihypertensive agents, antimicrobial agents, antimigraine agents, antimuscarinic agents, antineoplastic agents, antiparasitic agents, antiparkinson's agents, antiplatelet agents, antiprogestins, antithyroid agents, antitussives, antiviral agents, atypical antidepressants, azaspirodecanediones, barbiturates, benzodiazepines, benzothiadiazides, beta-adrenergic agonists, beta-adrenergic antagonists, selective beta-one-adrenergic antagonists, selective beta-two-adrenergic agonists, bile salts, agents affecting volume and composition of body fluids, butyrophenones, agents affecting calcification, calcium channel blockers, cardiovascular drugs, catecholamines and sympathomimetic drugs, cholinergic agonists, cholinesterase reactivators, dermatological agents, diphenylbutylpiperidines, diuretics, ergot alkaloids, estrogens, ganglionic blocking agents, ganglionic stimulating agents, hydantoins, agents for control of gastric acidity and treatment of peptic ulcers, hematopoietic agents, histamines, histamine antagonists, 5-hydroxytryptamine antagonists, drugs for the treatment of hyperlipoproteinemia, hypnotics and sedatives, immunosuppressive agents, laxatives, methylxanthines, moncamine oxidase inhibitors, neuromuscular blocking agents, organic nitrates, opiod analgesics and antagonists, pancreatic enzymes, phenothiazines, progestins, prostaglandins, agents for the treatment of psychiatric disorders, retinoids, sodium channel blockers, agents for spasticity and acute muscle spasms, succinimides, thioxanthines, thrombolytic agents, thyroid agents, tricyclic antidepressants, inhibitors of tubular transport of organic compounds, drugs affecting uterine motility, vasodilators, vitamins and the like, alone or in combination.

Administration of the drug according to the invention comprises administering at least one drug at a therapeutically effective rate to an area of a body surface or membrane and simultaneously administering a permeation enhancer of this invention to the area of the body surface or membrane at a rate sufficient to substantially increase the permeability of the area to the drug formulation.

According to the invention, the permeation enhancer and the drug to be delivered are placed in drug- and permeation enhancer-transmitting relationship to the appropriate body surface, preferably in a carrier therefor, and maintained in place for the desired period of time. The drug and permeation enhancer are typically dispersed within a physicochemically and biologically compatible matrix or carrier which may be applied directly to the body surface or skin as an ointment, gel, cream, suppository or sublingual or buccal tablet, for example, but are more preferably administered from a transdermal therapeutic delivery device as more fully described below. When used in the form of a liquid, ointment, cream, or gel applied directly to the skin, it is preferable, although not required, to occlude the site of administration. Such compositions can also contain other permeation enhancers, stabilizers, dyes, diluents, pigments, vehicles, inert fillers, excipients, gelling agents, vasoconstrictors, and other components of typical compositions as are known to the art.

The permeation enhancer of this invention has a permeation-enhancing effect on the transport of drugs through body surface tissues generally, in addition to the skin. However, because skin is one of the most effective body barriers to the permeation of foreign substances, the effect of the permeation enhancer composition on skin permeation makes it extremely useful in transdermal delivery. The following description of embodiments of the invention is therefore directed primarily to improving systemic delivery of these drugs by permeation through the skin.

The permeation enhancer is dispersed throughout the matrix or carrier, preferably at a concentration sufficient to provide permeation-enhancing amounts of enhancer in the reservoir throughout the anticipated administration period. Where there is an additional, separate permeation enhancer matrix layer as well, as in FIG. 2, the permeation enhancer normally is present in the separate reservoir in excess of saturation.

Figure 3:
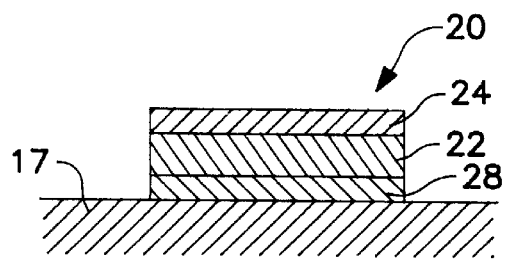
FIG. 3 is a cross-sectional view of yet another embodiment of a transdermal therapeutic drug delivery device which may be used in accordance with this invention.

One embodiment of a transdermal delivery device of the present invention is illustrated in FIG. 1. In FIG. 1, device 1 is comprised of a drug-and permeation enhancer-containing reservoir ("drug reservoir") 2 which is preferably in the form of a matrix containing the drug and the enhancer dispersed therein. A backing layer 3 is provided adjacent one surface of drug reservoir 2. Adhesive overlay 4 maintains the device 1 on the skin and may be fabricated together with, or provided separately from, the remaining elements of the device. With certain formulations, the adhesive overlay 4 may be preferable to an in-line contact adhesive, such as adhesive layer 28 as shown in FIG. 3. Backing layer 3 is preferably slightly larger than drug reservoir 2, and in this manner prevents the materials in drug reservoir 2 from adversely interacting with the adhesive in overlay 4. Reservoir 2 may be either saturated, unsaturated, or contain an amount of drug in excess of saturation. A strippable or removable liner 5 is also provided with device 1 and is removed just prior to application of device 1 to the skin.

Figure 2:
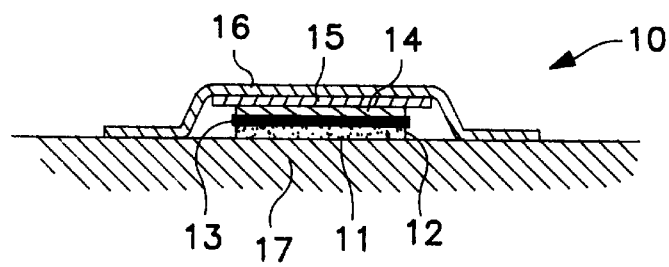
FIG. 2 is a cross-sectional view of another embodiment of a transdermal therapeutic drug delivery device which may be used in accordance with the present invention.

FIG. 2 illustrates another embodiment of the invention, device 10, shown in placement on the skin 17. In this embodiment, the transdermal delivery device 10 comprises a multi-laminate drug formulation/enhancer reservoir 11 having at least two zones 12 and 14. Zone 12 consists of a drug reservoir substantially as described with respect to FIG. 1. Zone 14 comprises a permeation enhancer reservoir which is preferably made from substantially the same matrix as is used to form zone 12. Zone 14 comprises the permeation enhancer dispersed throughout, preferably in excess of saturation. A rate-controlling membrane 13 for controlling the release rate of the permeation enhancer from zone 14 to zone 12 is placed between the two zones. A rate-controlling membrane (not shown) for controlling the release rate of the enhancer and/or drug from zone 12 to the skin may also optionally be utilized and would be present between the skin 17 and zone 12.

The rate-controlling membrane may be fabricated from permeable, semipermeable or microporous materials which are known in the art to control the rate of agents into and out of delivery devices and having a permeability to the permeation enhancer lower than that of zone 12. Suitable materials include, but are not limited to, polyethylene, polyvinyl acetate and ethylene vinyl acetate copolymers.

An advantage of the device described in FIG. 2 is that if zone 12 contains an excess of drug above saturation, the drug-loaded zone 12 is concentrated at the skin surface rather than throughout the entire mass of the reservoir 11. This functions to reduce the amount of drug in the device while maintaining an adequate supply of the permeation enhancer or mixture.

Superimposed over the drug formulation/enhancer-reservoir 11 of device 10 is a backing 15 and an adhesive overlay 16 as described above with respect to FIG. 1. In addition, a strippable liner (not shown) would preferably be provided on the device prior to use as described with respect to FIG. 1 and removed prior to application of the device 10 to the skin 17.

In the embodiments of FIGS. 1 and 2, the carrier or matrix material has sufficient viscosity to maintain its shape without oozing or flowing. If, however, the matrix or carrier is a low viscosity flowable material, the composition can be fully enclosed in a dense non-porous or microporous skin-contacting membrane, as known to the art from U.S. Pat. No. 4,379,454 (noted above), for example.

An example of a presently preferred transdermal delivery device is illustrated in FIG. 3. In FIG. 3, transdermal delivery device 20 comprises a drug reservoir 22 containing together the drug and the permeation enhancer. Reservoir 22 is preferably in the form of a matrix containing the drug and the enhancer dispersed therein. Reservoir 22 is sandwiched between a backing layer 24, which is impermeable to both the drug and the enhancer, and an in-line contact adhesive layer 28. In FIG. 3, the drug reservoir 22 is formed of a material, such as a rubbery polymer, that is sufficiently viscous to maintain its shape. The device 20 adheres to the surface of the skin 17 by means of the contact adhesive layer 28. The adhesive for layer 28 should be chosen so that it is compatible and does not interact with any of the drug or, in particular, the permeation enhancer. The adhesive layer 28 may optionally contain the permeation enhancer and/or drug. A strippable liner (not shown) is normally provided along the exposed surface of adhesive layer 28 and is removed prior to application of device 20 to the skin 17. In an alternative embodiment, a rate-controlling membrane (not shown) is present and the drug reservoir 22 is sandwiched between backing layer 24 and the rate-controlling membrane, with adhesive layer 28 present on the skin-facing side of the rate-controlling membrane.

Figure 4:
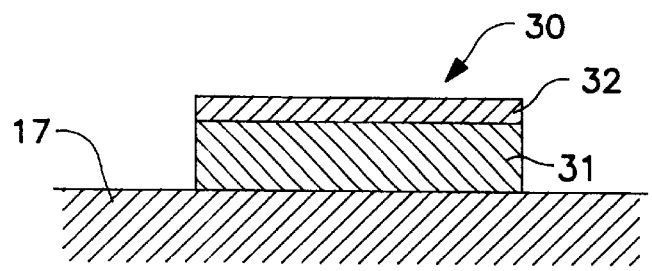
FIG. 4 is a cross-sectional view of yet another embodiment of a transdermal therapeutic drug delivery device which may be used in accordance with this invention.

FIG. 4 depicts another preferred embodiment of the present invention. Device 30 includes a matrix 31 comprising a pressure sensitive adhesive, preferably a hydrophobic pressure sensitive adhesive, having drug and the permeation enhancer dispersed therein and additionally includes a backing layer 32 to contain the agent and prevent its loss. Matrix 31 also preferably, but not necessarily, contains a water absorbing polymer to improve the long term wearability of the matrix system. A release liner (not shown in FIG. 4) may also be included and is removed prior to placing the device onto the skin 17.

Various materials suited for the fabrication of the various layers of the transdermal devices of FIGS. 1–4 are known in the art or are disclosed in the aforementioned transdermal device patents previously incorporated herein by reference.

The matrix making up the drug/permeation enhancer reservoir can be a gel or a polymer. Suitable materials should be compatible with the drug and enhancer and any other components in the system. The matrix may be aqueous or non-aqueous based. Aqueous formulations typically comprise water or water/ethanol and about 1–5 wt % of a gelling agent, an example being a hydrophilic polymer such as hydroxyethylcellulose or hydroxypropylcellulose. Typical non-aqueous gels are comprised of silicone fluid or mineral oil. Mineral oil based gels also typically contain 1–2 wt % of a gelling agent such as colloidal silicon dioxide. The suitability of a particular gel depends upon the compatibility of its constituents with the drug and the permeation-enhancing mixture in addition to any other components in the formulation. Suitable matrix materials include, without limitation, natural and synthetic rubbers or other polymeric material, thickened mineral oil, or petroleum jelly, for example.

Suitable non-aqueous based formulations for the reservoir matrix are well known in the transdermal drug delivery art, and examples are listed in the above-named patents previously incorporated herein by reference. A typical laminated system would consist essentially of a polymeric membrane and/or matrix such as ethylene vinyl acetate (EVA) copolymers, such as those described in U.S. Pat. No. 4,144,317, preferably having a vinyl acetate content in the range of from about 9% to about 60% and more preferably about 9% to 40% vinyl acetate. Polyisobutylene/oil polymers containing from 4–25% high molecular weight polyisobutylene and 20–81% low molecular weight polyisobutylene with the balance being an oil such as mineral oil or polyisobutynes may also be used as the matrix material.

In addition to a drug and permeation enhancer, which are essential to the invention, the matrix may also contain water absorbing polymers such as polyvinyl pyrrolidone, cross-linked polyvinyl pyrrolidone, polyaminoacrylates, and polyvinyl alcohol, stabilizers, dyes, pigments, inert fillers, tackifiers, excipients and other conventional components of transdermal delivery devices as are known in the art.

The amounts of the drug that are present in the therapeutic device, and that are required to achieve a therapeutic effect, depend on many factors, such as the minimum necessary dosage of the particular drug; the permeability of the matrix, of the adhesive layer and of the rate-controlling membrane, if present; and the period of time for which the device will be fixed to the skin. There is, in fact, no upper limit to the maximum amounts of drug present in the device. The minimum amount of each drug is determined by the requirement that sufficient quantities of drug must be present in the device to maintain the desired rate of release over the given period of application.

The drug is generally dispersed through the matrix at a concentration in excess of saturation in order to maintain unit activity throughout the administration period. The amount of excess is determined by the intended useful life of the system. However, the drug may be present at initial levels below saturation without departing from this invention. Generally, the drug may be present at initially subsaturated levels when: 1) the skin flux of the drug is sufficiently low such that the reservoir drug depletion is slow and small; 2) non-constant delivery of the drug is desired or acceptable; and/or 3) saturation or supersaturation of the reservoir is achieved in use by cosolvent effects which change the solubility of the drug in use such as by loss of a cosolvent or by migration of water into the reservoir.

The permeation enhancer is dispersed throughout the matrix, preferably at a concentration sufficient to provide permeation-enhancing concentrations of enhancer in the reservoir throughout the anticipated administration period.

In the present invention, the drug is delivered through the skin or other body surface at a therapeutically effective rate (that is, a rate that provides an effective therapeutic result) and the permeation enhancer is delivered at a permeation-enhancing rate (that is, a rate that provides increased permeability of the application site to the drug) for a predetermined time period.

A preferred embodiment of the present invention is a multilaminate such as that illustrated in FIG. 3 (either with or without a rate-controlling membrane) wherein reservoir 22 comprises, by weight, 30–90% polymer (preferably EVA with a vinyl acetate content of 40%), 0.01–40% drug, and 1–70% of a permeation enhancer according to Formula I. The in-line adhesive layer 28 contains an adhesive which is compatible with the permeation enhancer. In another preferred embodiment of the invention, a multilaminate such as that in FIG. 3 includes reservoir 22 comprising, by weight, 30–90% polymer (preferably EVA with a vinyl acetate content of 40%), 0.01–40% drug, 1–70% of a permeation enhancer according to Formula I, and 1–60% of a second permeation enhancer, preferably GML or ethanol.

The devices of this invention can be designed to effectively deliver a drug for an extended time period of up to 7 days or longer. Seven days is generally the maximum time limit for application of a single device because the skin site may be affected by a period of occlusion greater than 7 days, or other problems such as the system or edges of the system lifting off of the skin may be encountered over such long periods of application. Where it is desired to have drug delivery for greater than 7 days (such as, for example, when a hormone is being applied for a contraceptive effect), when one device has been in place on the skin for its effective time period, it is replaced with a fresh device, preferably on a different skin site.

The transdermal therapeutic devices of the present invention are prepared in a manner known in the art, such as by those procedures, for example, described in the transdermal device patents listed previously herein.

The following examples are offered to illustrate the practice of the present invention and are not intended to limit the invention in any manner.

EXAMPLE 1

Figure 5:
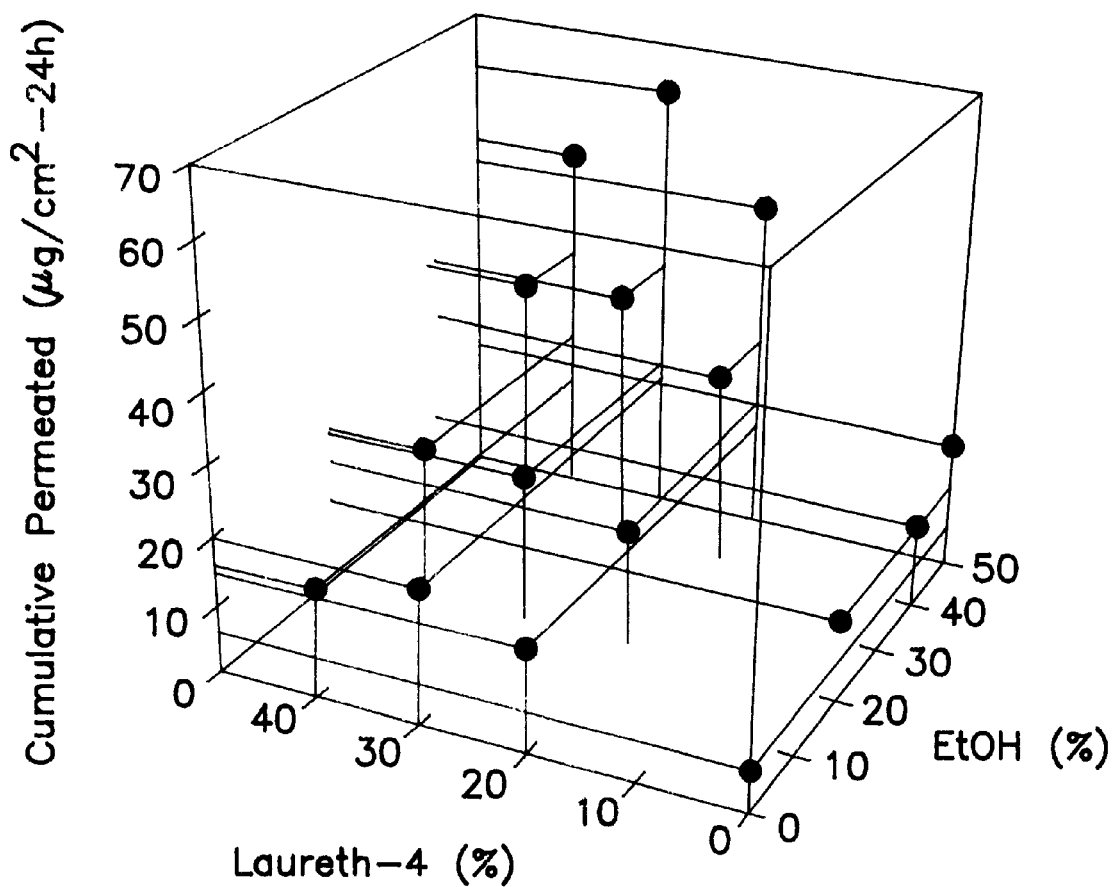
FIG. 5 is a plot showing the cumulative release of testosterone through human epidermis at 35° C., in vitro, from donor solutions containing varying amounts of laureth-4, alone or in combination with ethanol.

Various ethanol/tetraethylene glycol monododecyl ether (laureth-4) (Heterene Chemical Co., Patterson, N.J.) mixture donor compositions having different amounts of ethanol and laureth-4 were tested with testosterone to measure their effect upon drug flux across human cadaver epidermis at 35° C. All donor compositions were saturated with the drug. Test data were obtained using a 1.13 cm$^2$ wet-wet horizontal flux cell with 0.2 ml donor solution and 20 ml receptor solution (pH 7.4 phophate buffer, 0.05 M). Total drug permeated was measured and the results are presented in FIG. 5. As seen in FIG. 5, 30 wt % laureth-4 alone exhibited about a four fold increase in testosterone permeation compared to the sample without any permeation enhancer.

TABLE 1

Measured and predicted cumulative release
($\mu$g/cm$^2$ · 24 hr) from donor solutions
of various ethanol and laureth-4 content

| laureth-4 wt % | ethanol wt % | measured release | predicted release |
|---|---|---|---|
| 0 | 0 | 5 | — |
| 20 | 0 | 15 | — |
| 30 | 0 | 20 | — |
| 40 | 0 | 16 | — |
| 0 | 20 | 15 | — |
| 0 | 40 | 18 | — |
| 0 | 50 | 21 | — |
| 20 | 20 | 20 | 30 |
| 20 | 40 | 32 | 33 |
| 20 | 50 | 50 | 36 |
| 30 | 20 | 25 | 35 |
| 30 | 40 | 40 | 38 |
| 30 | 50 | 60 | 41 |
| 40 | 20 | 26 | 31 |
| 40 | 40 | 39 | 34 |
| 40 | 50 | 52 | 37 |

Table 1 lists the formulations including the amounts of ethanol and laureth-4 and the observed cumulative release of testosterone over a 24 hour period. Table 1 also provides a predicted cumulative release of testosterone which is the sum of that observed from the formulations including the corresponding amounts of laureth-4 or ethanol alone. As seen from Table 1, the enhancement of testosterone permeation in the presence of both ethanol and laureth-4 showed a more than additive effect of the results obtained from the sum of the cumulative amount permeated from each of these enhancers individually when the ethanol was present at about 40 wt % or greater.

EXAMPLE 2

Transdermal systems were prepared to measure the flux of oxybutynin through human epidermis. The oxybutynin/permeation enhancer reservoir was prepared by mixing ethylene vinyl acetate copolymer having a vinyl acetate content of 40 percent ("EVA 40", U.S.I. Chemicals, Illinois) in an internal mixer (Brabender type mixer) until the EVA 40 pellets fused. Oxybutynin, glycerol monolaurate (Danisco Ingredients USA, Inc., New Century, Kans.) and either diethylene glycol monododecyl ether (laureth-2) (Heterene Chemical Co., Patterson, N.J.) or lauryl lactate (ISP Van Dyk, Bellevue, N.J.) were then added. The oxybutynin/enhancer reservoir formulation is shown in Table 2.

The mixture was blended, cooled, and calendered to a 5 mil thick film. The drug reservoir film was then laminated to a Sontara® (DuPont, Wilmington, Del.) backing on its skin distal surface and a Celgard® (Hoescht Celanese, Charlotte, N.C.) microporous polypropylene membrane on its skin facing surface. An acrylic contact adhesive (MSP041991P, 3M) was then laminated to the microporous polypropylene membrane. The laminate was then cut into 1.98 cm$^2$ circles using a stainless steel punch and placed in a 35° C. oven to equilibrate. Systems were then masked to prevent any part of the system other than the skin contacting surface to be exposed to the receptor solution when performing the skin flux experiments.

TABLE 2

Drug Reservoir Formulation (wt %)

| Oxybutynin | GML | lauryl lactate | laureth-2 | EVA 40 |
|---|---|---|---|---|
| 20 | 25 | 12 | — | 43 |
| 20 | 25 | — | 12 | 43 |

The in vitro transdermal oxybutynin permeation rates through the epidermis of two human skin donors from the systems described above were determined. For each system tested, the release liner was removed and the oxybutynin-releasing surface was centered and placed against the stratum corneum side of a disc of human epidermis which had been blotted dry just prior to use. The excess epidermis was wrapped around the device so that none of the device edge was exposed to the receptor solution.

The assembly was then attached to the flat side of a Teflon® holder of a release rate rod using wire and nylon mesh. The rod with the system attached was placed into a 50 cc test tube filled with a known volume of receptor solution (0.05M phosphate solution, pH 6.0). Constant vertical stirring was accomplished by attaching the rod to a crossrod connected to an agitator that reciprocates the rod and system vertically in the test tube. The receptor solution was maintained at 35° C.

Figure 6:
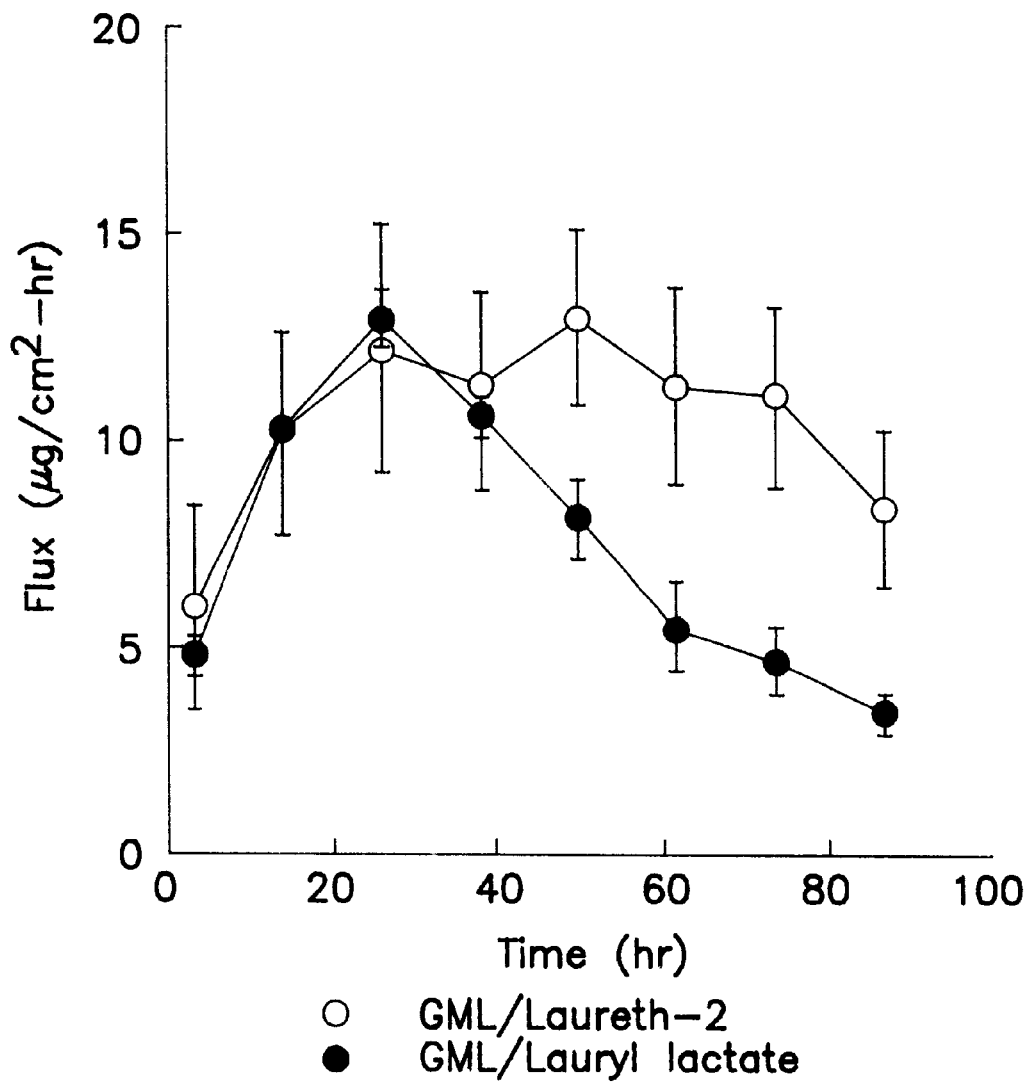
FIG. 6 is a plot showing the flux of oxybutynin through human epidermis at 35° C., in vitro, from an EVA matrix system containing laureth-2 or lauryl lactate, each in combination with GML.
Figure 7:
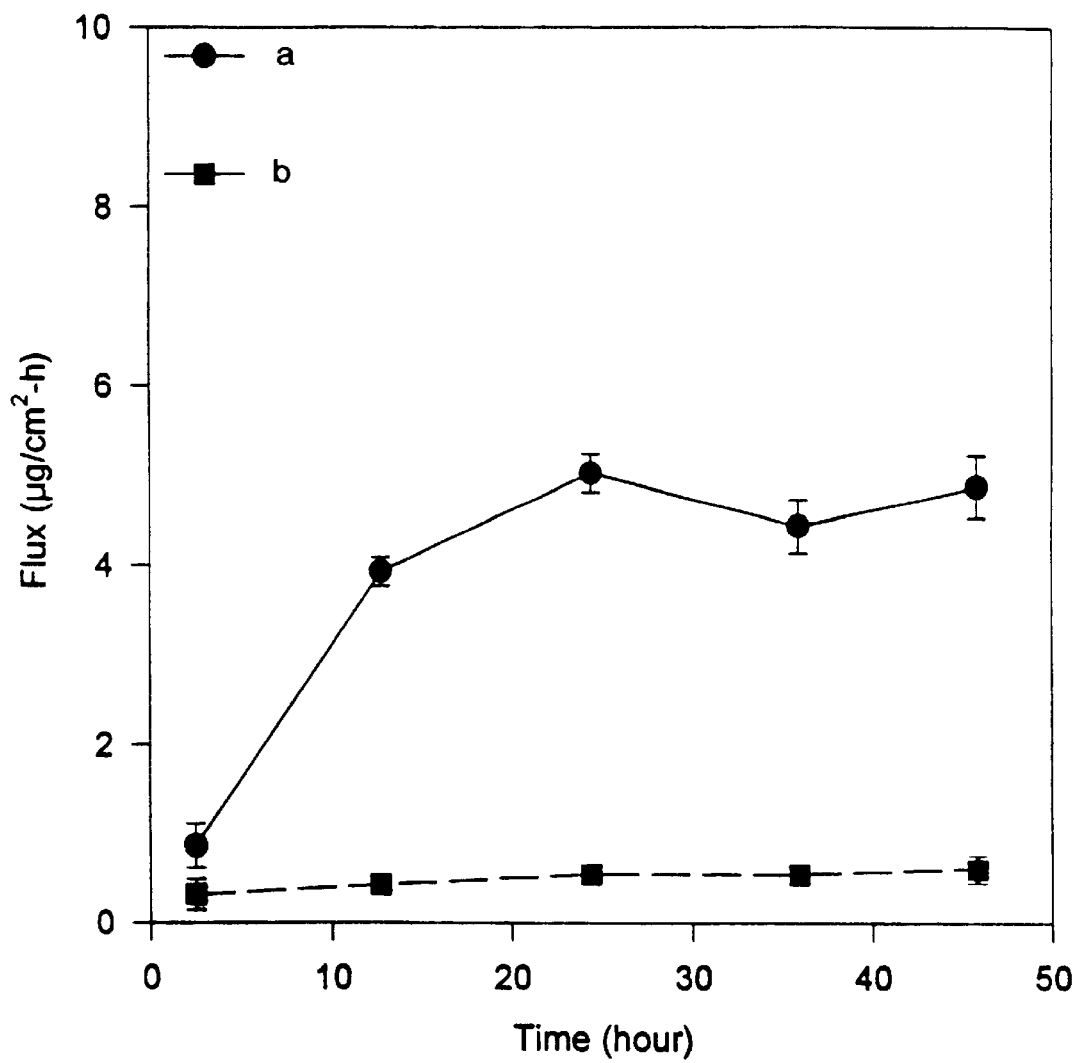
FIGS. 7–18 are plots of the flux of various drugs through human epidermis at 35° C., in vitro, showing the increased skin permeability obtained from various permeation-enhancing mixtures of this invention.
Figure 8:
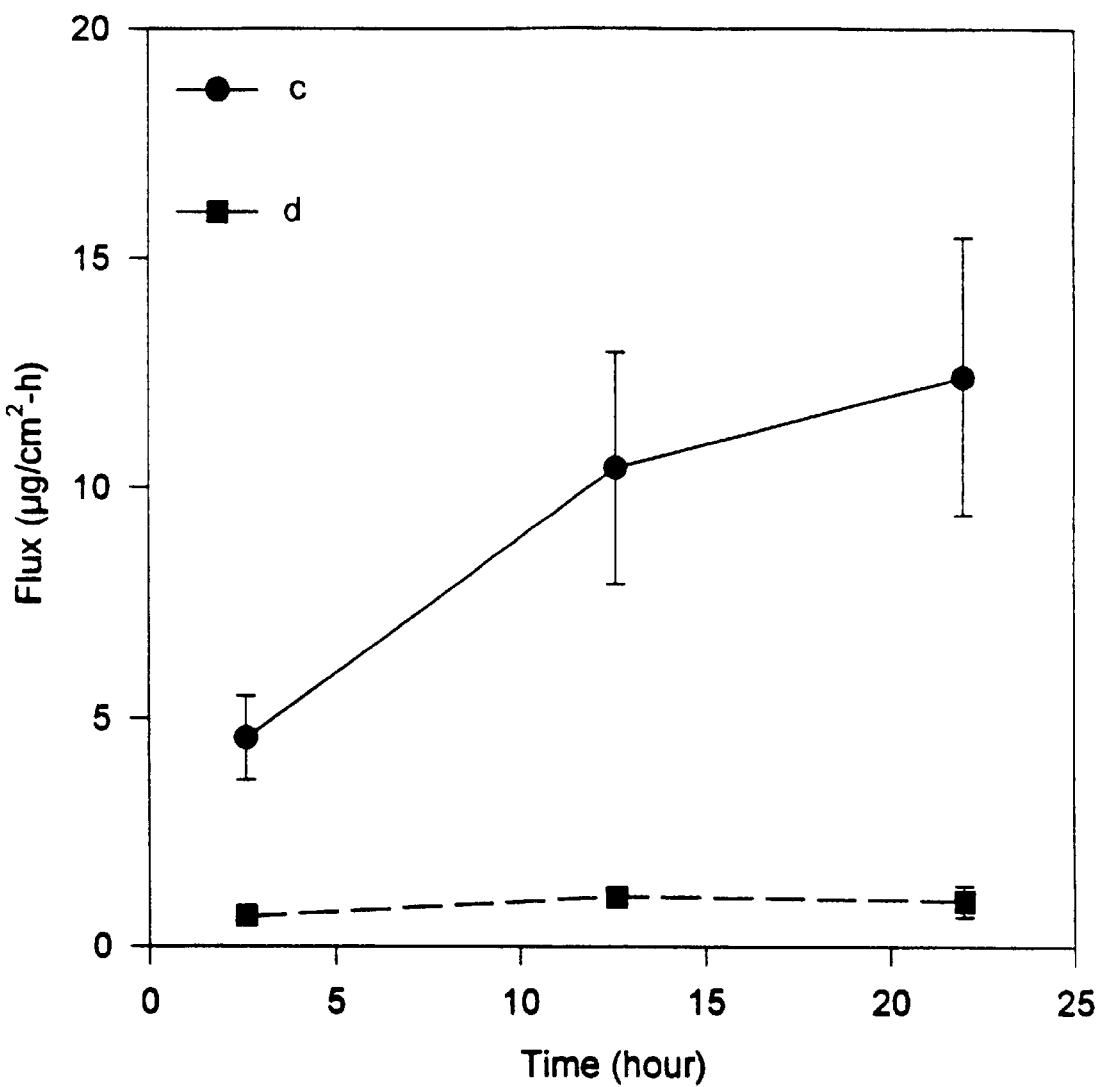
Figure 9:
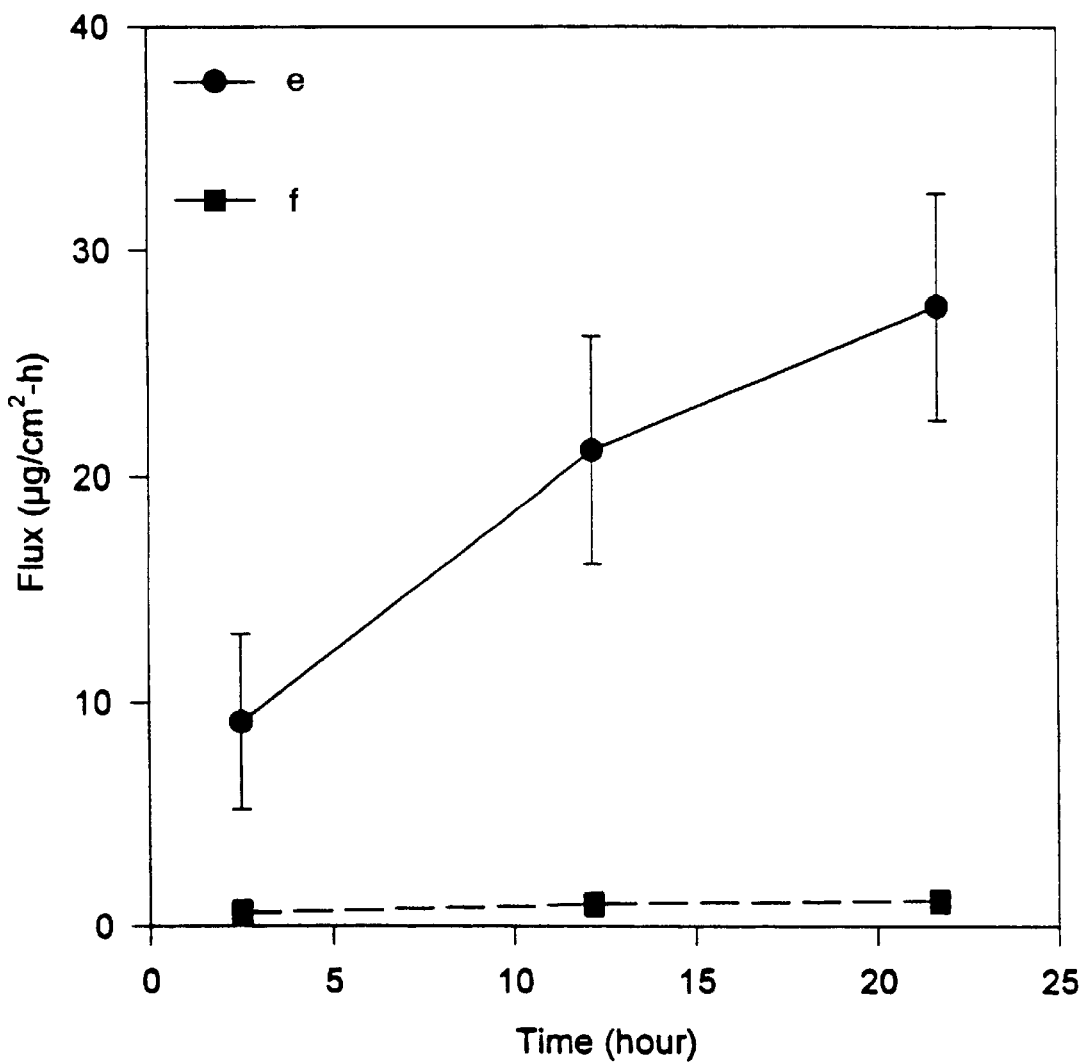
Figure 10:
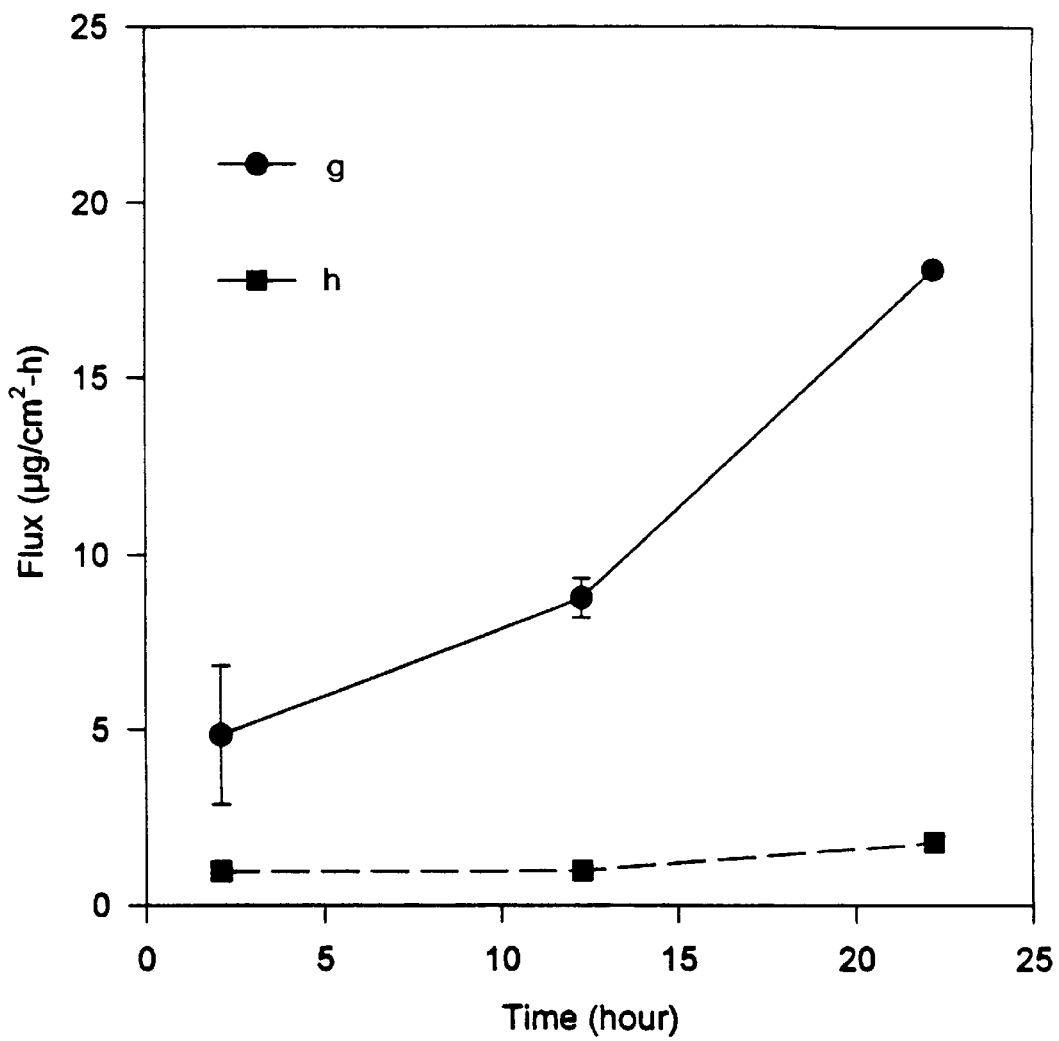
Figure 11:
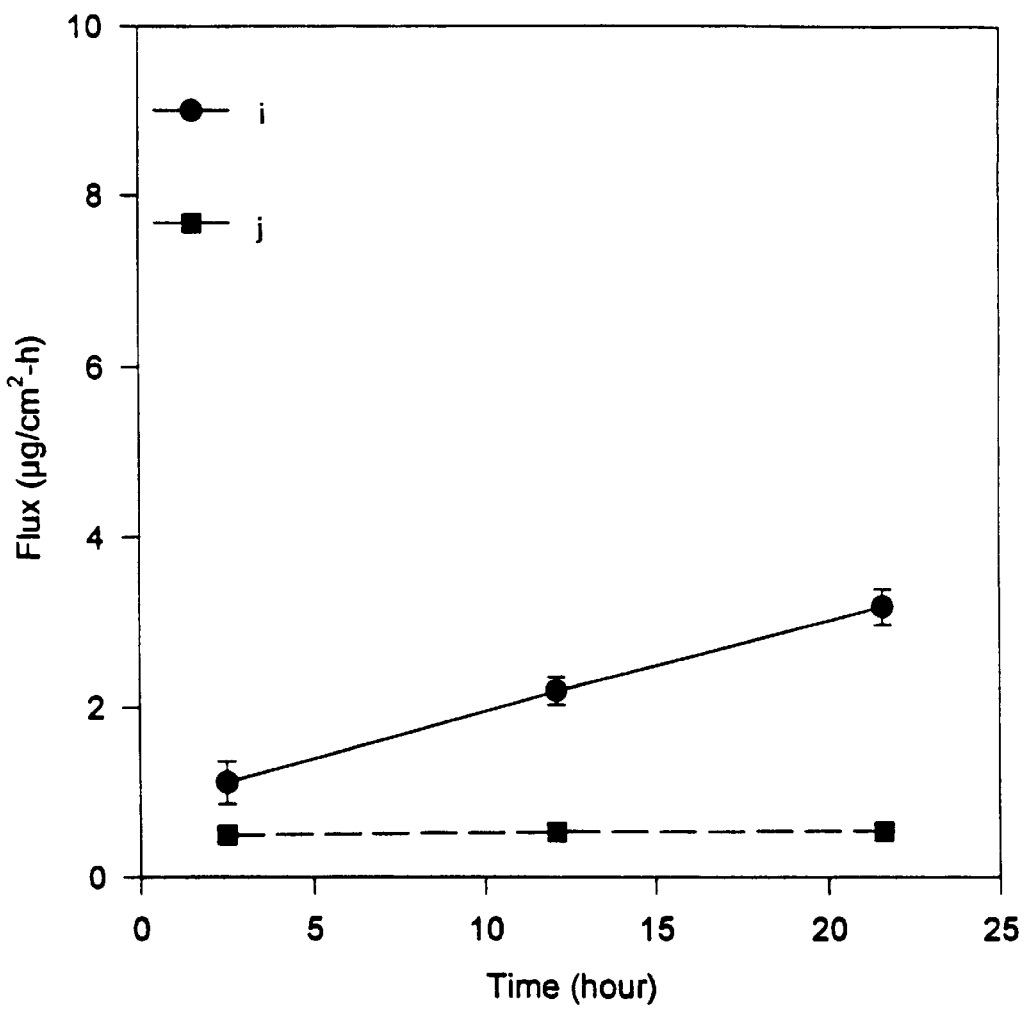
Figure 12:
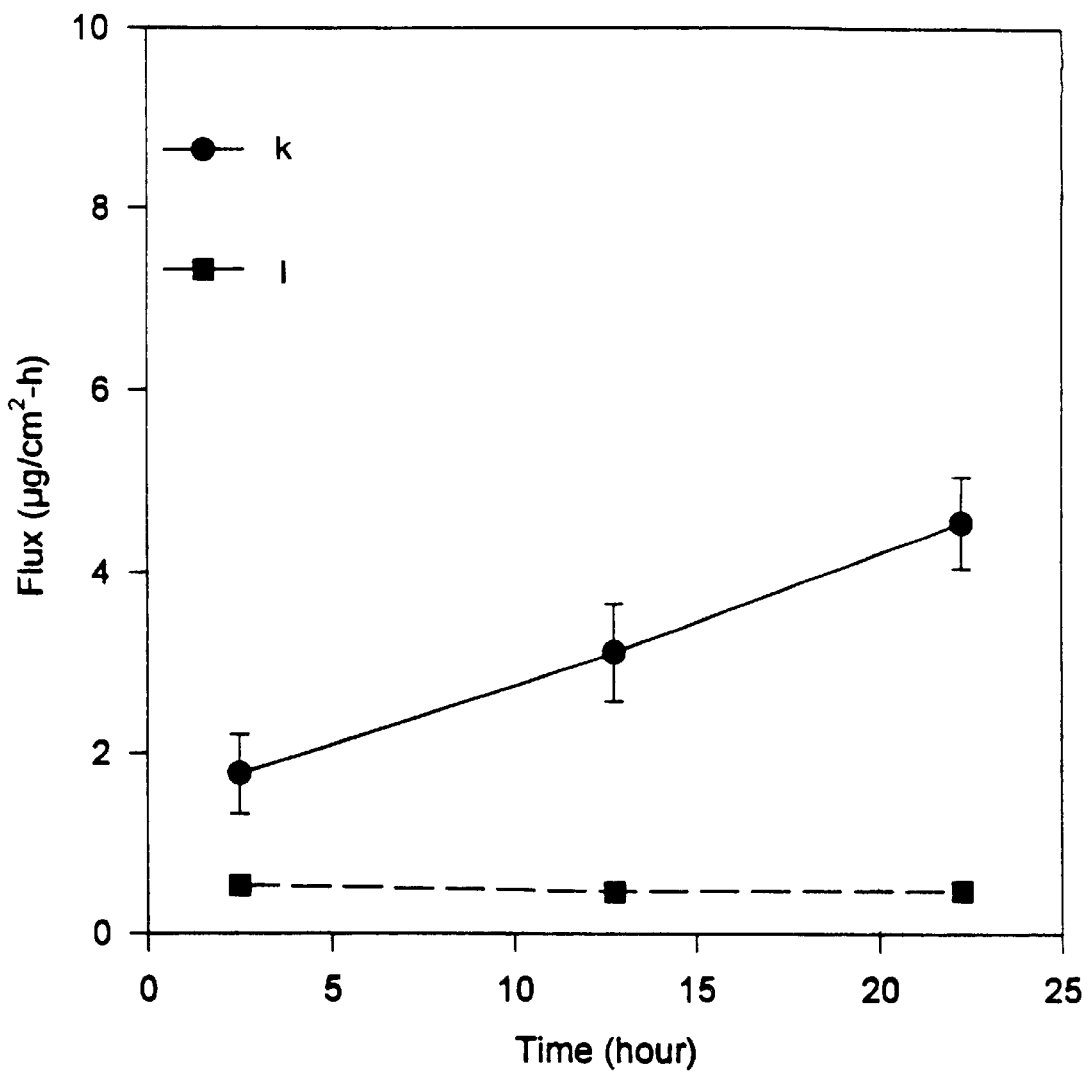
Figure 13:
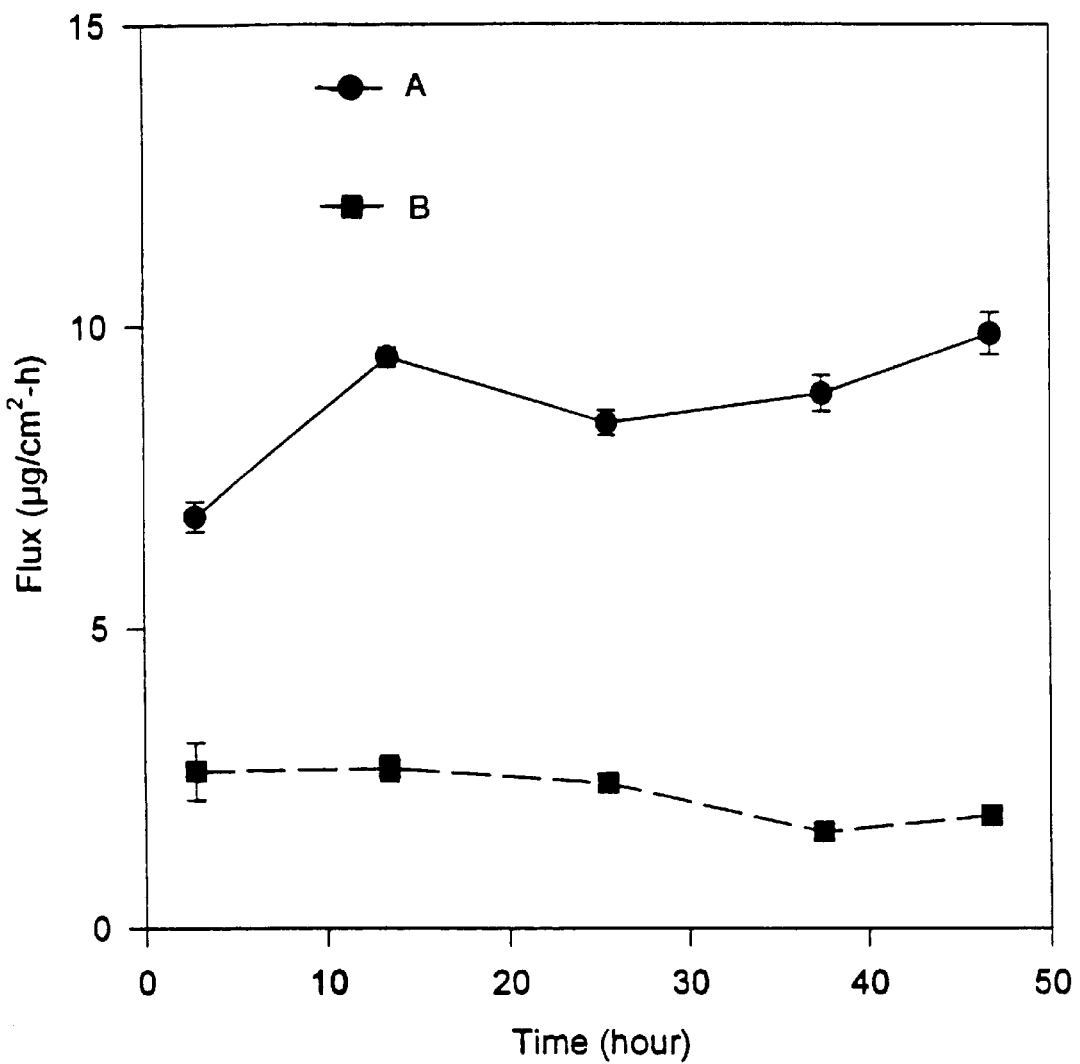
Figure 14:
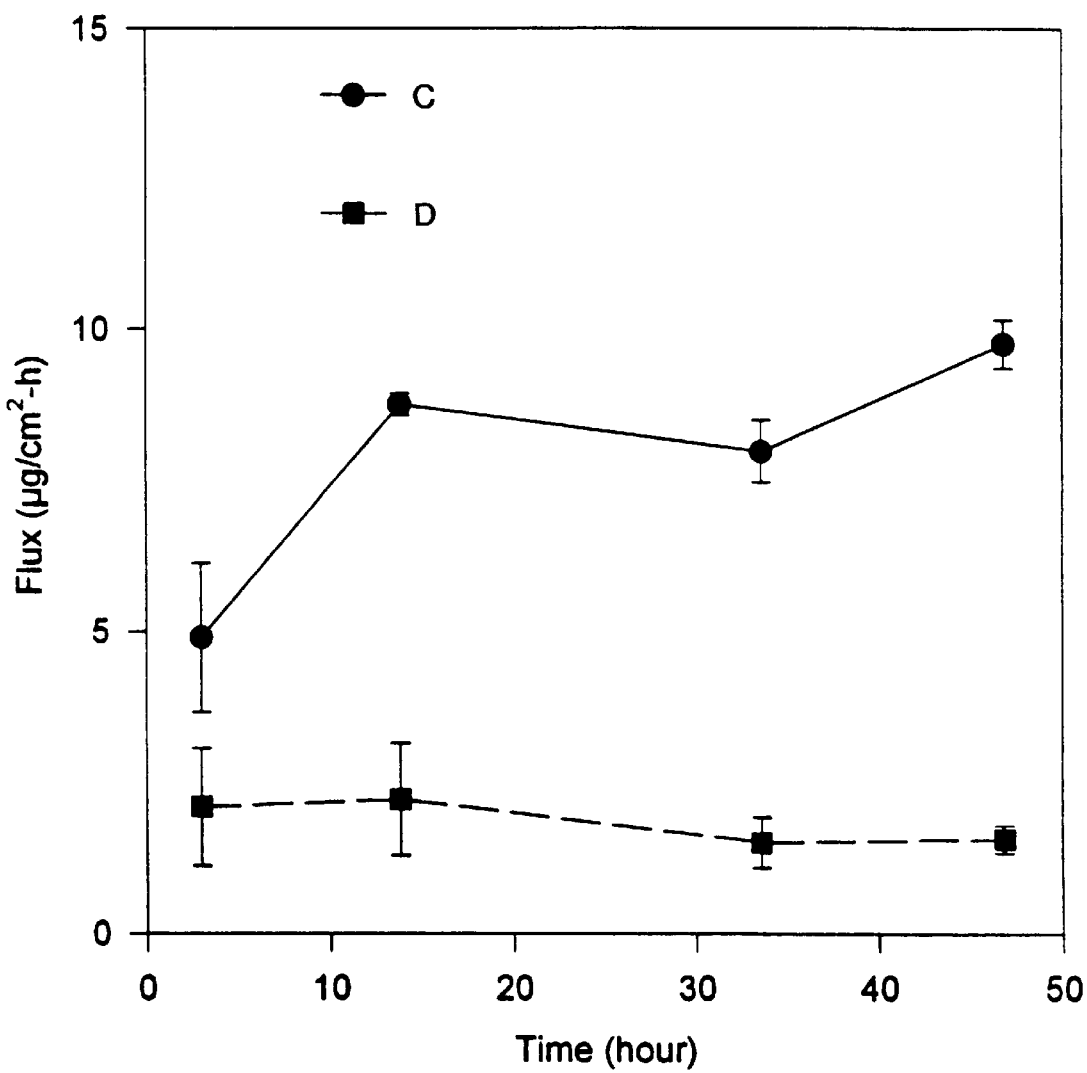
Figure 15:
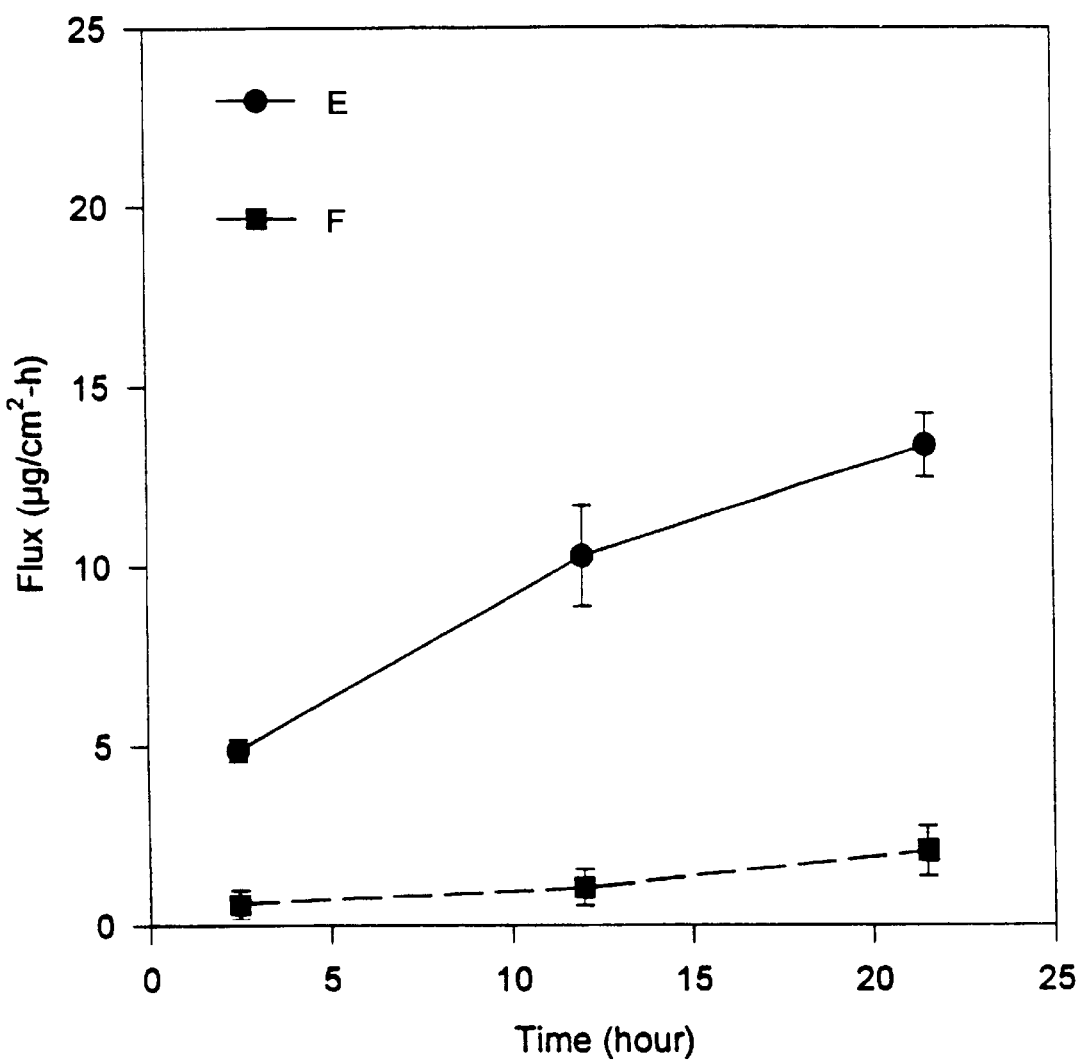
Figure 16:
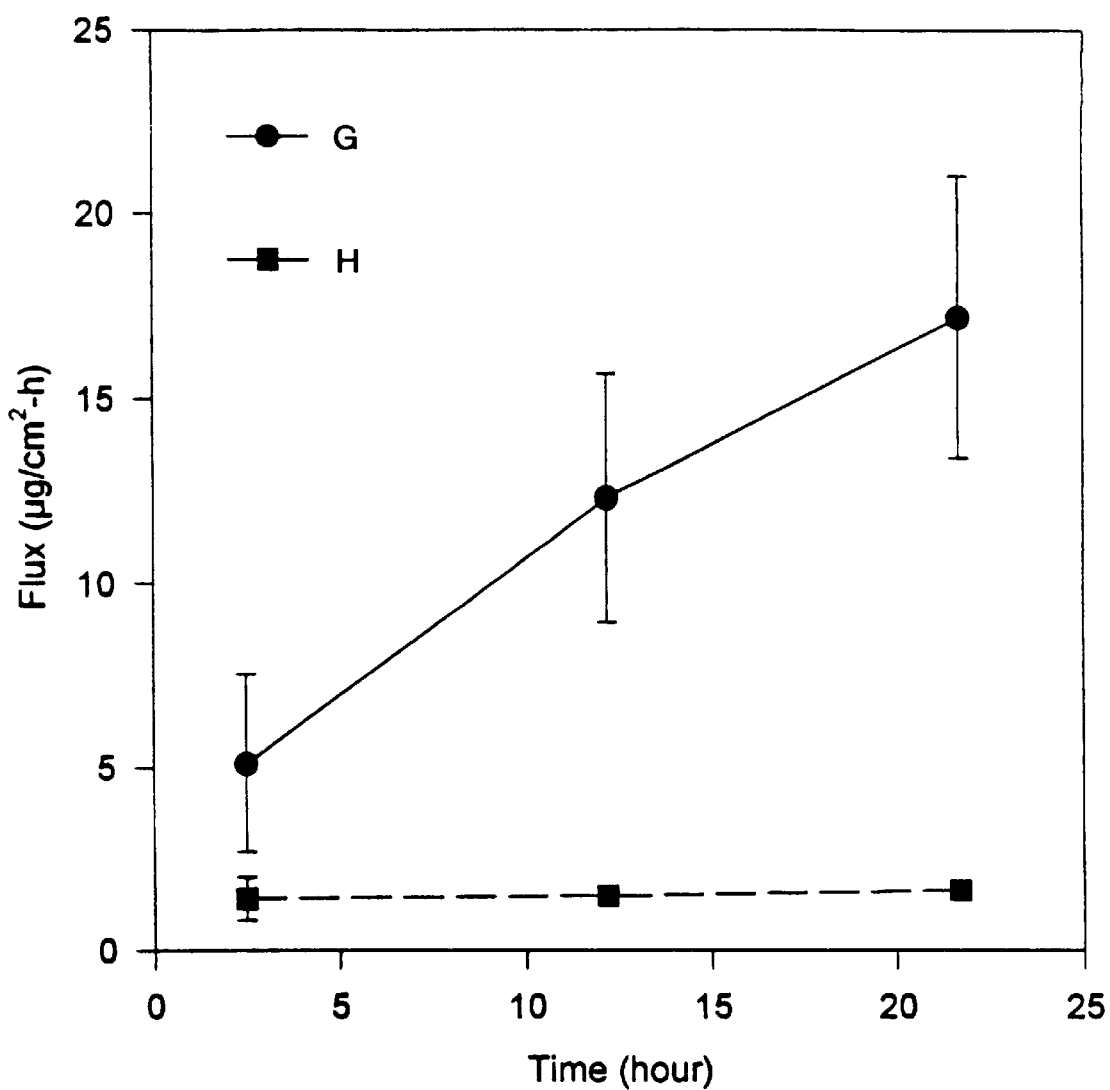
Figure 17:
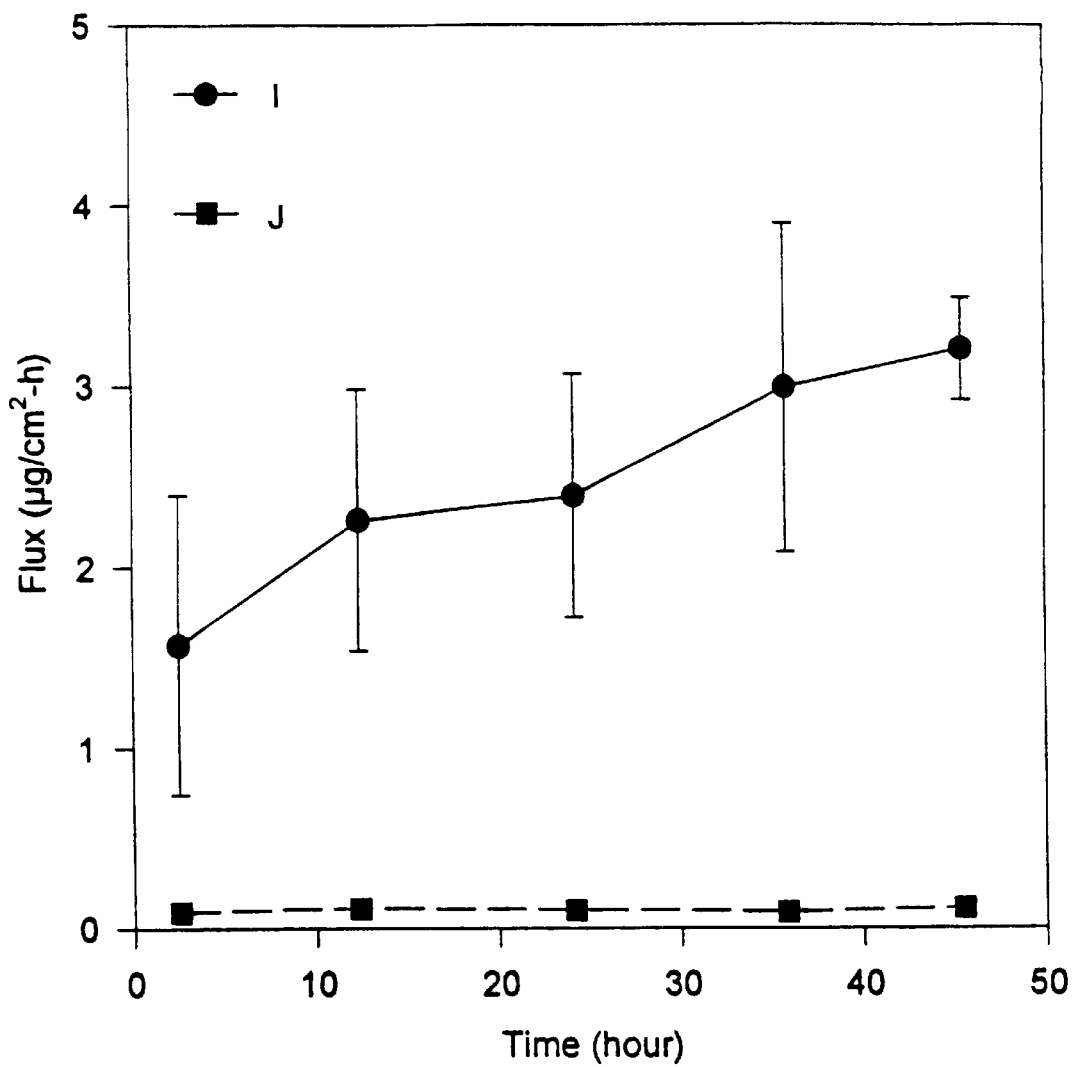
Figure 18:
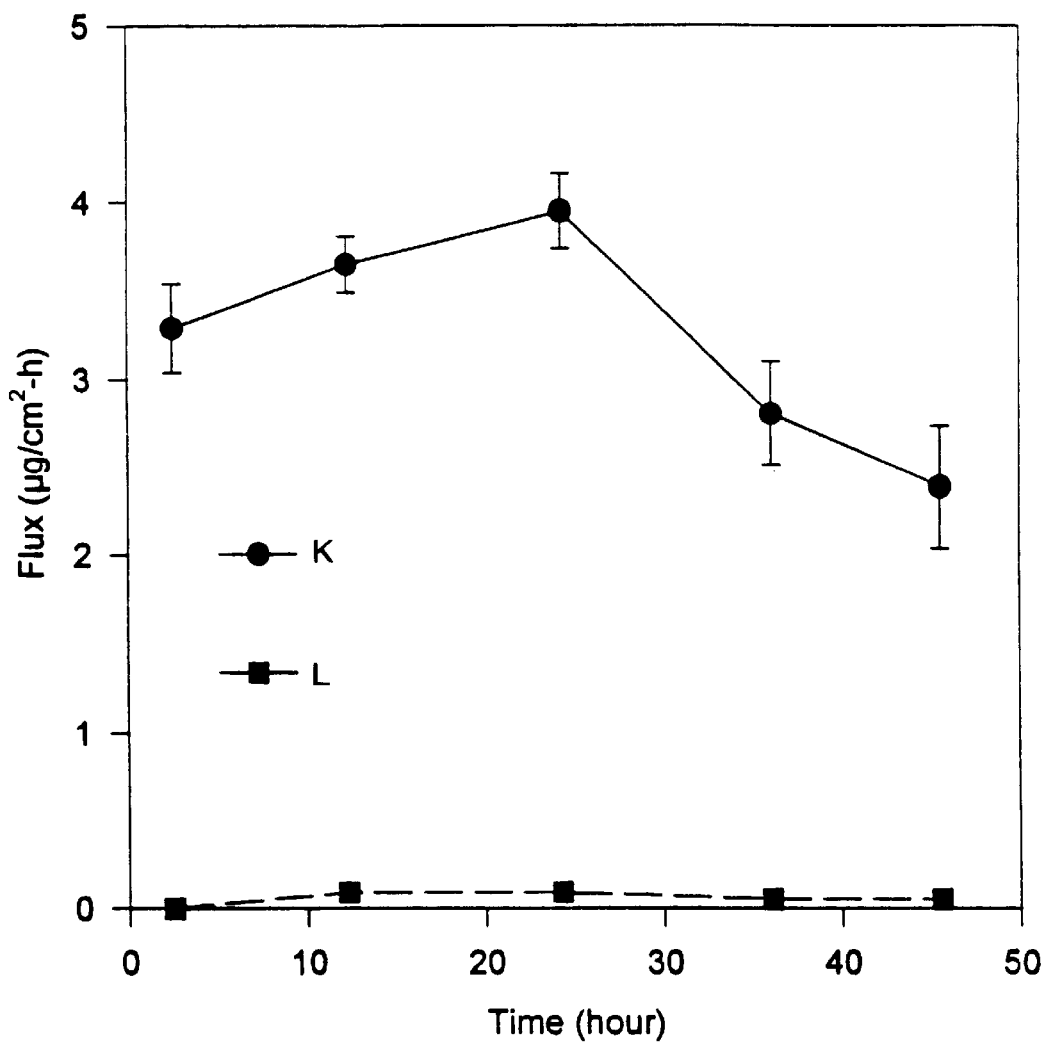

At given time intervals, the entire receptor solution was removed from the test tube and replaced with an equal volume of fresh receptor solution previously equilibrated at 35° C. The receptor solutions were stored in capped vials at 4° C. until assayed for oxybutynin content by HPLC. From the drug concentration and the volume of receptor solution, the area of permeation and the time interval, the flux of the drug through the epidermis was calculated as follows: (drug concentration×volume of receptor solution)/(area×time)= flux ($\mu$g/cm$^2$·hr). The results are depicted in FIG. 6, which shows that the system comprising the GML/laureth-2 mixture resulted in the longer maintenance of a higher flux than the GML/lauryl lactate system.

EXAMPLE 3

Control formulations containing drug in a matrix of EVA 40 were prepared by dissolving the drug and EVA 40 in tetrohyfrofuran (THF). The solution was poured onto an FCD/polyester release liner to evaporate. The dried material was then pressed to 4–5 mils thickness between two sheets of FCD/polyester release liner at 75° C. The resulting film was heat-laminated to an impermeable backing (Medpar or Scotchpak, for example), and 1.6 cm² discs were punched out or die-cut from the laminate.

Test formulations containing laureth-2 benzoate (Bernel Chemical Co., Englewood, N.J.) or laureth-2 acetate (Phoenix Chemical Co., Inc., Somerville, N.J.) in addition to the drug and EVA 40 were prepared by dissolving the necessary components in THF and following the same procedures as for the control formulations. The compositions of the test formulations and controls are shown in Table 3.

TABLE 3

Laureth-2 acetate and Laureth-2 benzoate Test and Control Formulations

| Formulation | Drug | wt % | Permeation Enhancer | wt % | EVA 40 wt % |
|---|---|---|---|---|---|
| a | oxybutynin | 25 | laureth-2 benzoate | 25 | 50 |
| b | oxybutynin | 25 | — | — | 75 |
| c | melatonin | 10 | laureth-2 acetate | 25 | 65 |
| d | metatonin | 10 | — | — | 90 |
| e | ketorolac | 7 | laureth-2 benzoate | 25 | 68 |
| f | ketorolac | 10 | — | — | 90 |
| g | ketorolac | 7 | laureth-2 acetate | 25 | 68 |
| h | ketorolac | 10 | — | — | 90 |
| i | testosterone | 10 | laureth-2 benzoate | 25 | 65 |
| j | testosterone | 2 | — | — | 98 |
| k | testosterone | 10 | laureth-2 acetate | 25 | 65 |
| l | testosterone | 2 | — | — | 98 |

The in vitro transdermal flux of oxybutynin, melatonin, ketorolac, and testosterone with either laureth-2 acetate or laureth-2 benzoate was compared to the no-enhancer control using the in vitro skin flux experiment described in Example 2 above. The results are depicted in FIGS. 7–12, which show that both laureth-2 acetate and laureth-2 benzoate increased significantly the skin permeability to these drugs.

EXAMPLE 4

Control formulations containing drug in a matrix of EVA 40 were prepared as described in Example 3. Test formulations containing laureth-3 carboxylic acid (L-3 carboxylic acid) (Huls America Inc., Piscataway, N.J.) or laureth-5 carboxylic acid (L-5 carboxylic acid) ) (Huls America Inc., Piscataway, N.J.) in addition to the drug and EVA 40 were prepared by dissolving the necessary components in THF and following the same procedures as for the control formulations. The compositions of the test formulations and controls are shown in Table 4.

TABLE 4

Laureth-3 carboxylic acid and Laureth-5 carboxylic acid Test and Control Formulations

| Formulation | Drug | wt % | Permeation Enhancer | wt % | EVA 40 wt % |
|---|---|---|---|---|---|
| A | oxybutynin | 25 | L-3 carboxylic acid | 25 | 50 |
| B | oxybutynin | 25 | — | — | 75 |
| C | oxybutynin | 10 | L-5 carboxylic acid | 25 | 65 |
| D | oxybutynin | 10 | — | — | 90 |
| E | ketorolac | 7 | L-3 carboxylic acid | 25 | 68 |
| F | ketorolac | 10 | — | — | 90 |
| G | ketorolac | 7 | L-5 carboxylic acid | 25 | 68 |
| H | ketorolac | 10 | — | — | 90 |

TABLE 4-continued

Laureth-3 carboxylic acid and Laureth-5 carboxylic acid Test and Control Formulations

| Formulation | Drug | wt % | Permeation Enhancer | wt % | EVA 40 wt % |
|---|---|---|---|---|---|
| I | alprazolam | 15 | L-3 carboxylic acid | 25 | 60 |
| J | alprazolam | 15 | — | — | 85 |
| K | alprazolam | 15 | L-5 carboxylic acid | 25 | 60 |
| L | alprazolam | 15 | — | — | 85 |

The in vitro transdermal flux of oxybutynin, alprazolam, and ketorolac, with either L-5 carboxylic acid or L-3 carboxylic acid was compared to the no-enhancer control using the in vitro skin flux experiment described in Example 2 above. The results are depicted in FIGS. 13–18, which show that both L-5 carboxylic acid and L-3 carboxylic acid increased significantly the skin permeability to these drugs.

This invention has been described in detail with particular reference to certain preferred embodiments thereof, but it will be understood that variations and modifications can be effected within the spirit and scope of the invention.

What is claimed is:

1. A composition of matter for increasing the permeability of a body surface or membrane to at least one drug comprising said drug in combination with a permeation enhancer selected from the group consisting of alkyl or aryl carboxylic acid esters of polyethyleneglycol monoalkyl ether, and polyethyleneglycol alkyl carboxymethyl ethers, said permeation enhancer present in a permeation-enhancing amount sufficient to substantially increase the permeability of the body surface or membrane to at least one drug in order to deliver said drug to an individual at a therapeutically effective rate.

2. A composition according to claim 1 wherein the permeation enhancer and at least one drug are dispersed within a pharmaceutically acceptable carrier.

3. A composition according to claim 1 wherein the permeation enhancer is a carboxylic acid ester of polyethyleneglycol monolauryl ether.

4. A composition according to claim 3 wherein the permeation enhancer is selected from diethylene glycol monododecyl ether-acetate and diethylene glycol monododecyl ether-benzoate.

5. A composition according to claim 1 wherein the permeation enhancer is a polyethyleneglycol lauryl carboxymethyl ether.

6. A composition according to claim 5 wherein the permeation enhancer is selected from triethylene glycol monododecyl ether-carboxylic acid and polyethylene glycol monododecyl ether-carboxylic acid.

7. A composition according to claim 1 wherein the permeation enhancer is combined with a permeation-enhancing amount of one or more permeation enhancers selected from monoglycerides or mixtures of monoglycerides of fatty acids, lauramide diethanolamine, lower $C_{1-4}$ alcohols, alkyl laurates, acyl lactylates, dodecyl acetate, and $C_{10}$–$C_{20}$ fatty acid esters.

8. A composition according to claim 7 wherein the permeation enhancer is combined with a permeation-enhancing amount of one or more permeation enhancers selected from glycerol monolaurate, glycerol monooleate, glycerol monolinoleate, lauramide diethanolamine, ethanol, methyl laurate, caproyl lactylic acid, lauroyl lactylic acid, dodecyl acetate, and lauryl lactate.

9. A composition according to claim 7 wherein the permeation enhancer is combined with a permeation-enhancing amount of glycerol monolaurate.

10. A device for the transdermal administration of at least one drug to an individual at a therapeutically effective rate, by permeation through a body surface or membrane, comprising:
(a) a reservoir comprising at least one drug and a permeation enhancing-amount of a permeation enhancer selected from the group consisting of alkyl of aryl carboxylic acid esters of polythyleneglycol monoalkyl ether, and polyethyleneglycol alkyl carboxymethyl ethers said permeation enhancer present in a permeation-enhancing amount sufficient to substantially increase the permeability of the body surface or membrane to at least one drug in order to deliver said drug to an individual at a therapeutically effective rate; and
(b) means for maintaining said reservoir in drug- and permeation enhancer-transmitting relation with the body surface or membrane, wherein said drug is delivered to a patient at a therapeutically effective rate.

11. A device according to claim 10 wherein the permeation enhancer is a carboxylic acid ester of polyethyleneglycol monolauryl ether.

12. A device according to claim 11 wherein the permeation enhancer is selected from diethylene glycol monododecyl ether-acetate and diethylene glycol monododecyl ether-benzoate.

13. A device according to claim 10 wherein the permeation enhancer is a polyethyleneglycol lauryl carboxymethyl ether.

14. A device according to claim 13 wherein the permeation enhancer is selected from triethylene glycol monododecyl ether-carboxylic acid and polyethylene glycol monododecyl ether-carboxylic acid.

15. A device according to claim 10 wherein the permeation enhancer is combined with a permeation-enhancing amount of one or more of the permeation enhancers selected from monoglycerides or mixtures of monoglycerides of fatty acids, lauramide diethanolamine, lower $C_{1-4}$ alcohols, alkyl laurates, acyl lactylates, dodecyl acetate, and $C_{10}$–$C_{20}$ fatty acid esters.

16. A device according to claim 15 wherein the permeation enhancer is combined with a permeation-enhancing amount of one or more permeation enhancers selected from glycerol monolaurate, glycerol monooleate, glycerol monolinoleate, lauramide diethanolamine, ethanol, methyl laurate, caproyl lactylic acid, lauroyl lactylic acid, dodecyl acetate, and lauryl lactate.

17. A device according to claim 15 wherein the permeation enhancer is combined with a permeation-enhancing amount of glycerol monolaurate.

18. A device according to claim 10 wherein the drug is selected from testosterone, nandrolone, alprazolam, oxybutynin, ketorolac, and melatonin.

19. A device for the transdermal administration of at least one drug to an individual at a therapeutically effective rate, by permeation through a body surface or membrane, comprising:
(a) a first reservoir comprising at least one drug and a permeation-enhancing amount of a permeation enhancer selected from the group consisting of alkyl or aryl carboxylic acid esters of polyethyleneglycol monoalkyl ether, and polyethyleneglycol alkyl carboxymethyl ethers
(b) a second reservoir adjacent the skin-distal surface of the first reservoir comprising an additional amount of said permeation enhancer and substantially free of said drug in excess of saturation;
(c) means for maintaining said first and second reservoirs in drug- and permeation enhancer-transmitting relation with the body surface or membrane, wherein the drug is delivered to a patient at a therapeutically effective rate.

20. A device according to claim 19 further comprising a rate controlling membrane positioned between the first and second reservoirs.

21. A device according to claim 19 wherein the permeation enhancer is a carboxylic acid ester of polyethyleneglycol monolauryl ether.

22. A device according to claim 21 wherein the permeation enhancer is selected from diethylene glycol monododecyl ether-acetate and diethylene glycol monododecyl ether-benzoate.

23. A device according to claim 19 wherein the permeation enhancer is a polyethyleneglycol lauryl carboxymethyl ether.

24. A device according to claim 23 wherein the permeation enhancer is selected from triethylene glycol monododecyl ether-carboxylic acid and polyethylene glycol monododecyl ether-carboxylic acid.

25. A device according to claim 24 wherein the permeation enhancer is combined with a permeation-enhancing amount of one or more of the permeation enhancers selected from monoglycerides or mixtures of monoglycerides of fatty acids, lauramide diethanolamine, lower $C_{1-4}$ alcohols, alkyl laurates, acyl lactylates, dodecyl acetate, and $C_{10}$–$C_{20}$ fatty acid esters.

26. A device according to claim 25 wherein the permeation enhancer is combined with a permeation-enhancing amount of one or more permeation enhancers selected from glycerol monolaurate, glycerol monooleate, glycerol monolinoleate, lauramide diethanolamine, ethanol, methyl laurate, caproyl lactylic acid, lauroyl lactylic acid, dodecyl acetate, and lauryl lactate.

27. A device according to claim 25 wherein the permeation enhancer is combined with a permeation-enhancing amount of glycerol monolaurate.

28. A device according to claim 19 wherein the drug is selected from testosterone, nandrolone, alprazolam, oxybutynin, ketorolac, and melatonin.

29. A method for the transdermal administration of at least one drug to an individual, at a therapeutically effective rate, by permeation through a body surface or membrane, comprising:
simultaneously administering, to the body surface or membrane:
(a) at least one drug; and
(b) a permeation enhancer selected from the group consisting of alkyl or aryl carboxylic acid esters of polyethyleneglycol monoalkyl ether, and polyethylene glycol akyl carboxymethyl ethers, at a rate sufficient to substantially increase the permeability of the body surface or membrane to the drug in order to deliver said drug to an individual at a therapeutically effective rate.

30. A method according to claim 29 further comprising simultaneously coadministering, at a permeation-enhancing rate, one or more of the permeation enhancers selected from monoglycerides or mixtures of monoglycerides of fatty acids, lauramide diethanolamine, lower $C_{1-4}$ alcohols, alkyl laurates, acyl lactylates, dodecyl acetate, and $C_{10}$–$C_{20}$ fatty acid esters.

31. A method according to claim 29 wherein the permeation enhancer is selected from diethylene glycol monododecyl ether, tetraethylene glycol monododecyl ether, diethylene glycol monododecyl ether acetate, diethylene glycol monododecyl ether benzoate, triethylene glycol monododecyl ether carboxylic acid, and polyethylene glycol monododecyl ether carboxylic acid.

32. A method according to claim 30 wherein the permeation enhancer is combined with a permeation-enhancing amount of one or more permeation enhancers selected from glycerol monolaurate, glycerol monooleate, glycerol monolinoleate, lauramide diethanolamine, ethanol, methyl laurate, caproyl lactylic acid, lauroyl lactylic acid, dodecyl acetate, and lauryl lactate.

33. A method according to claim 30 wherein the permeation enhancer is combined with a permeation-enhancing amount of glycerol monolaurate.

34. A method according to claim 29 wherein the drug is selected from testosterone, alprazolam, oxybutynin, ketorolac, melatonin, and nandrolone.

* * * * *